US012371648B2

(12) United States Patent
Sakai et al.

(10) Patent No.: US 12,371,648 B2
(45) Date of Patent: Jul. 29, 2025

(54) ATOMIZATION DEVICE AND CULTURE DEVICE

(71) Applicant: PHC Corporation, Ehime (JP)

(72) Inventors: Yuta Sakai, Saitama (JP); Hironobu Sekine, Gunma (JP); Hikaru Aoki, Gunma (JP); Hiroki Hirai, Kagawa (JP)

(73) Assignee: PHC CORPORATION, Tokyo (JP)

( * ) Notice: Subject to any disclaimer, the term of this patent is extended or adjusted under 35 U.S.C. 154(b) by 675 days.

(21) Appl. No.: 17/724,030

(22) Filed: Apr. 19, 2022

(65) Prior Publication Data

US 2022/0243166 A1 Aug. 4, 2022

Related U.S. Application Data

(63) Continuation of application No. PCT/JP2020/038225, filed on Oct. 9, 2020.

(30) Foreign Application Priority Data

Oct. 30, 2019 (JP) ................................ 2019-197487

(51) Int. Cl.

| | |
|---|---|
| *C12M 1/12* | (2006.01) |
| *A61L 2/22* | (2006.01) |
| *A61L 2/26* | (2006.01) |
| *B05B 17/00* | (2006.01) |

(52) U.S. Cl.

CPC ............... *C12M 37/00* (2013.01); *A61L 2/22* (2013.01); *A61L 2/26* (2013.01); *B05B 17/0646* (2013.01); *A61L 2202/15* (2013.01)

(58) Field of Classification Search

None

See application file for complete search history.

(56) References Cited

U.S. PATENT DOCUMENTS

| | | | |
|---|---|---|---|
| 9,027,548 B2 | 5/2015 | Borgschulte et al. | |
| 2008/0073447 A1 | 3/2008 | Wang et al. | |
| 2011/0284656 A1 | 11/2011 | Kambayashi et al. | |
| 2013/0079733 A1* | 3/2013 | Burt | B08B 3/12 239/102.1 |
| 2014/0017132 A1 | 1/2014 | Nakata et al. | |

(Continued)

FOREIGN PATENT DOCUMENTS

| | | |
|---|---|---|
| CA | 3056275 A1 | 9/2018 |
| JP | 2011-036771 A | 2/2011 |

(Continued)

OTHER PUBLICATIONS

Stanford, webpage titled “Managing CF”, <https://med.stanford.edu/cfcenter/education/english/ManagingCF.html>, cached by Internet Archive Jul. 15, 2019 (Year: 2019).*

(Continued)

*Primary Examiner* — Holly Kipouros
(74) *Attorney, Agent, or Firm* — Rimon P.C.

(57) ABSTRACT

An atomization device according to the present invention is provided with: a main body part which has a container space that contains a hydrogen peroxide solution; and a diaphragm which is provided with through holes where the hydrogen peroxide solution contained in the container space passes, and which atomizes the hydrogen peroxide solution passing through the through holes.

10 Claims, 5 Drawing Sheets

(56) References Cited

U.S. PATENT DOCUMENTS

| | | |
|---|---|---|
| 2015/0054182 A1 | 2/2015 | Kawashima et al. |
| 2015/0102124 A1 | 4/2015 | Hu et al. |
| 2015/0209456 A1* | 7/2015 | Turbett ............... A61L 2/07 |
| | | 422/26 |
| 2015/0238993 A1 | 8/2015 | Hsieh et al. |
| 2016/0022928 A1 | 1/2016 | Cheng et al. |
| 2019/0247529 A1* | 8/2019 | Shane ............... A61L 2/22 |

FOREIGN PATENT DOCUMENTS

| | | |
|---|---|---|
| JP | 2014-176730 A | 9/2014 |
| JP | 2015-157275 A | 9/2015 |
| JP | 2017-060864 A | 3/2017 |
| JP | 2018-117587 A | 8/2018 |

OTHER PUBLICATIONS

Extended European Search Report dated Oct. 25, 2022 issued in the corresponding European Patent Application No. 20880354.4.
International Search Report dated Dec. 22, 2020 issued in International Patent Application No. PCT/JP2020/038225, with English translation.

* cited by examiner

ATOMIZATION DEVICE AND CULTURE DEVICE

CROSS-REFERENCE OF RELATED APPLICATIONS

This application is a Continuation of International Patent Application No. PCT/JP2020/038225, filed on Oct. 9, 2020, which in turn claims the benefit of Japanese Patent Application No. 2019-197487, filed on Oct. 30, 2019, the entire disclosures of which Applications are incorporated by reference herein.

TECHNICAL FIELD

The present disclosure relates to an atomization device and a culture device.

BACKGROUND ART

In the related art, an ultrasonic atomizer that atomizes decontamination liquid is known as a device for decontaminating the inside of a culture device for culturing objects such as cells and microorganisms.

For example, the $CO_2$ incubator disclosed in PTL 1 is equipped with the ultrasonic atomizer disclosed in Patent Document 2. The ultrasonic atomizer disclosed in PTL 2 atomizes the decontamination liquid at the liquid level of the decontamination liquid by vibrating a piezoelectric element with ultrasonic waves.

CITATION LIST

Patent Literature

PTL 1
 Japanese Patent Application Laid-Open No. 2017-60864
PTL 2
 Japanese Patent Application Laid-Open No. 2011-36771

SUMMARY OF INVENTION

Technical Problem

However, when an ultrasonic atomizer such as the one disclosed in PTL 2 is used, the decontamination liquid droplets generated tend to be large, making it difficult for the decontamination liquid to diffuse. Therefore, it was difficult to spread the decontamination liquid to every corner of the interior of the culture device.

An object of the present disclosure is to provide an atomization device that can generate smaller droplets and a culture device including the atomization device.

Solution to Problem

An atomization device according to the present disclosure includes: a main body part including a storage space configured to store hydrogen peroxide solution; a diaphragm configured to atomize the hydrogen peroxide solution that passes through a through hole, the through hole being formed in the diaphragm and a part through which the hydrogen peroxide solution stored in the storage space passes, the diaphragm including an outer surface facing a side opposite to a storage space side, the diaphragm being disposed on a front side of the main body part such that the outer surface faces an obliquely upper side with respect to a horizontal surface; and an inner cylindrical part located between the storage space and the diaphragm and including a supply path connected to the storage space, the supply path being a part through which the hydrogen peroxide solution flowing from the storage space toward the diaphragm passes. An upper end line connecting an uppermost end of an inner peripheral surface of the inner cylindrical part at each position from an end portion on a diaphragm side to an end portion on a storage space side has a shape whose height increases as a distance to the storage space decreases.

A culture device according to the present disclosure includes the above-described atomization device

Advantageous Effects of Invention

According to the present disclosure, it is possible to provide a atomization device that can generate smaller droplets and a culture device including the atomization device.

DESCRIPTION OF EMBODIMENTS

An embodiment the present disclosure is described in detail below with reference to the accompanying drawings. Note that the embodiment described below is an example, and the present disclosure is not limited to the embodiment.

Figure 1:
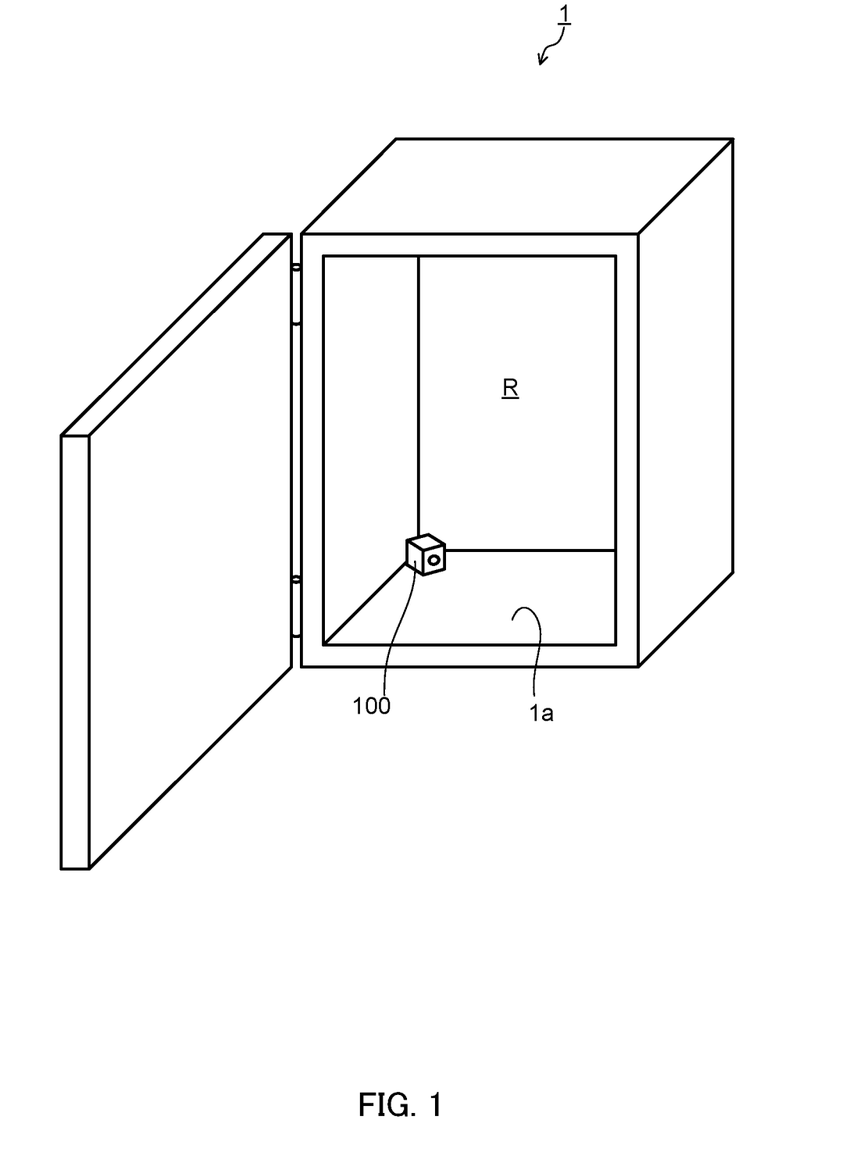
FIG. 1 is a schematic view illustrating an example of a culture device according to the present disclosure.

FIG. 1 is a schematic view illustrating an example of culture device 1 according to the present disclosure.

In culture chamber R as its internal space, culture device 1 can perform growing of plants, culture of plants cells, tissues, and organs, breeding and growing of insects and the like. In the following description, the object of culture, breeding and growing the like by the culture device 1 is simply referred to as object.

When culture device 1 performs culture, breeding, growing and the like of the above-described object, culture chamber R must be kept clean. Culture device 1 performs decontamination operation of culture chamber R by performing a predetermined operation.

Atomization device 100 is disposed in culture chamber R when culture device 1 performs the decontamination operation. Note that 1a in FIG. 1 represents a surface (i.e., installation surface) where atomization device 100 is disposed. Atomization device 100 stores in its inside decontamination liquid used for the decontamination operation, and in the decontaminate operation of culture device 1, atomization device 100 emits the decontamination liquid to culture chamber R in a mist form by atomizing the decontamination liquid. Note that atomization device 100 may be provided to culture device 1.

Figure 2:
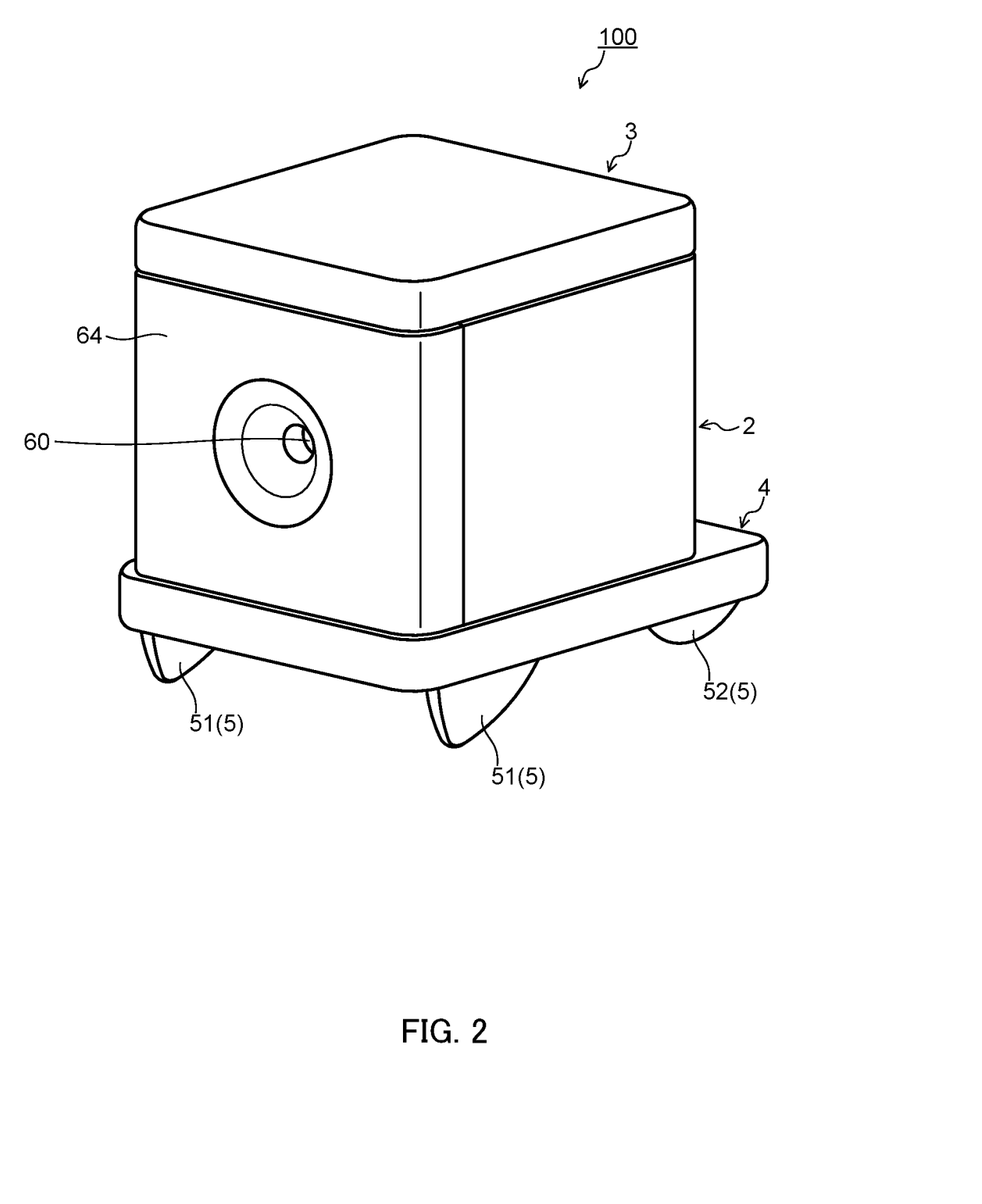
FIG. 2 is a perspective view illustrating an example of an external appearance of an atomization device according to the present disclosure.
Figure 3:
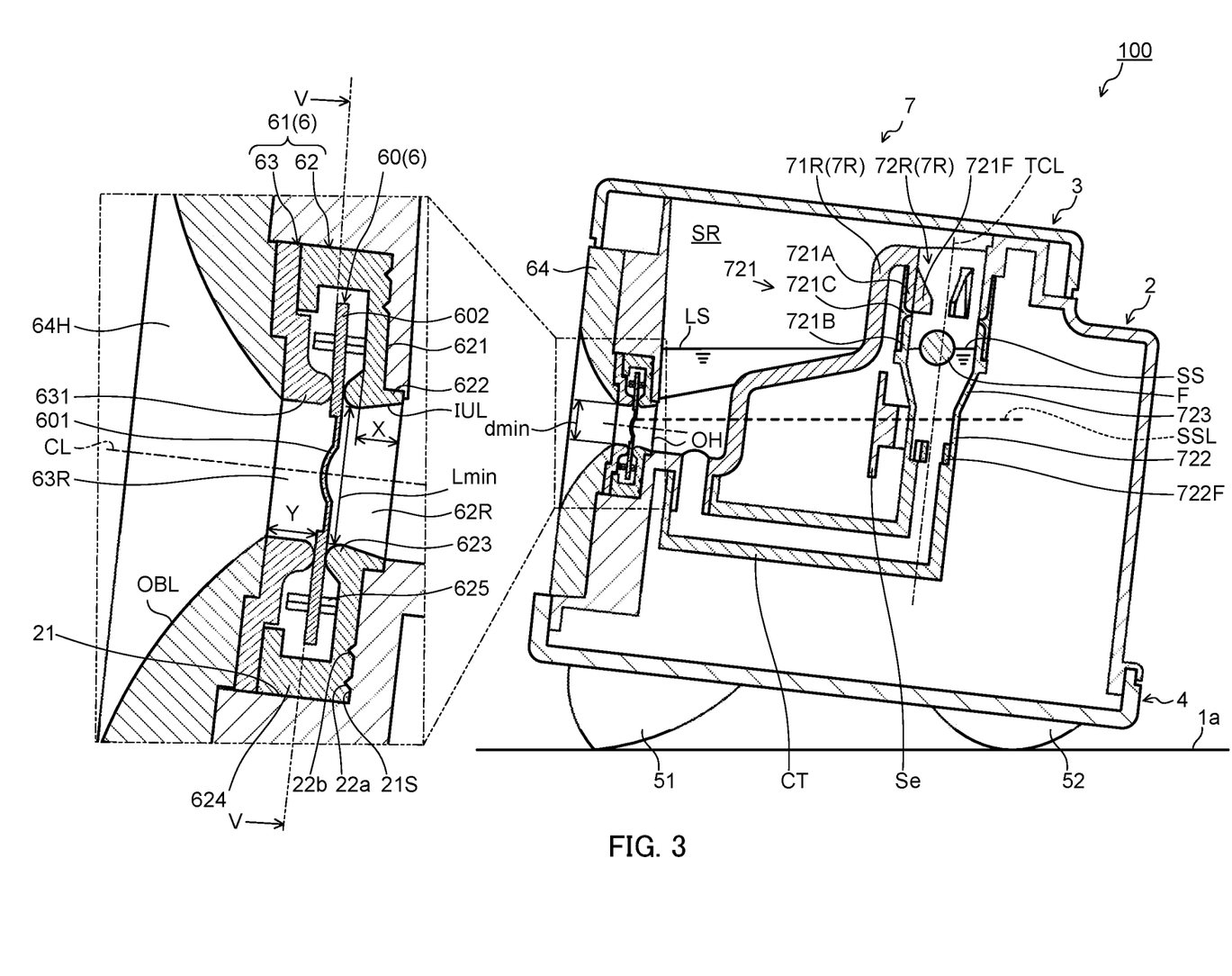
FIG. 3 is a longitudinal sectional view of the atomization device according to the present disclosure taken along a vertical plane.
Figure 4:
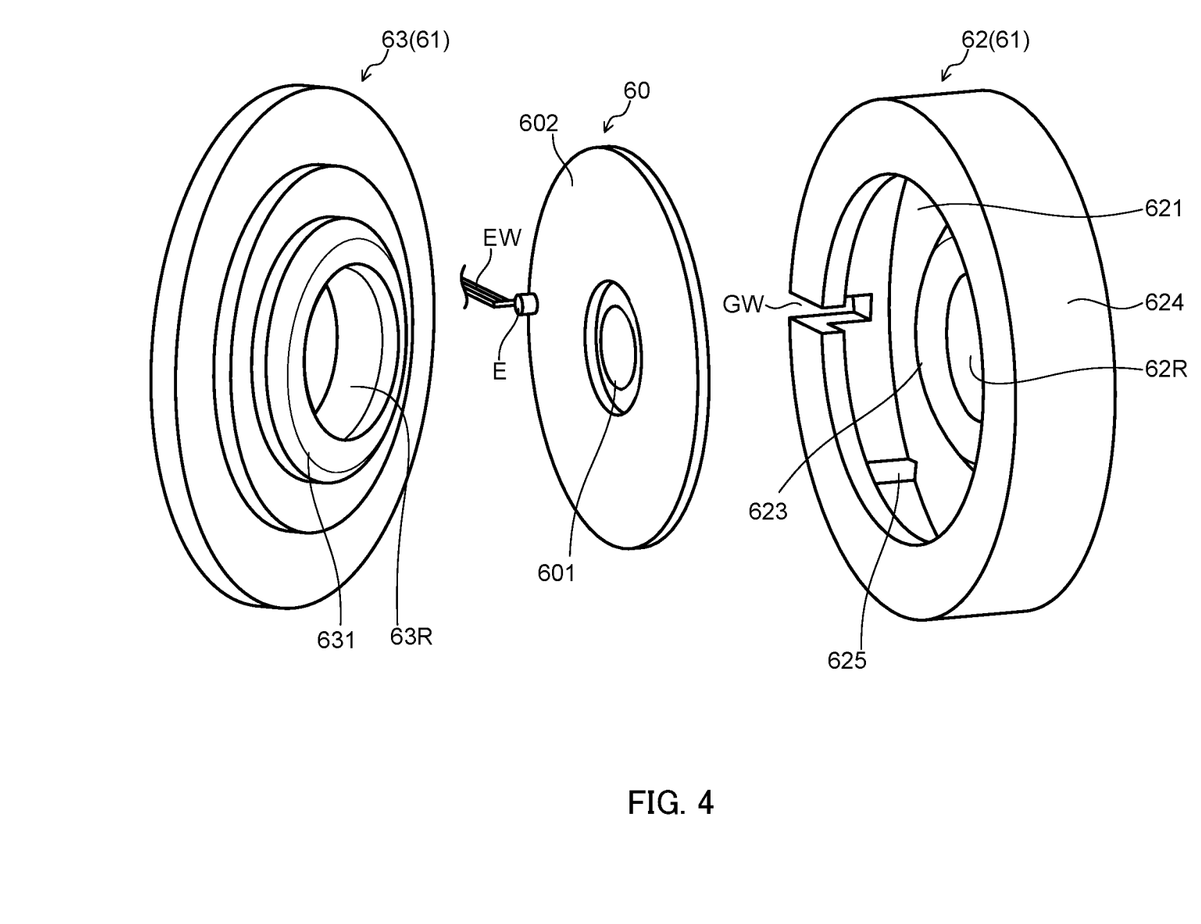
FIG. 4 is a diagram illustrating an example of an external appearance of a diaphragm and a holding member provided in the atomization device according to the present disclosure.
Figure 5:
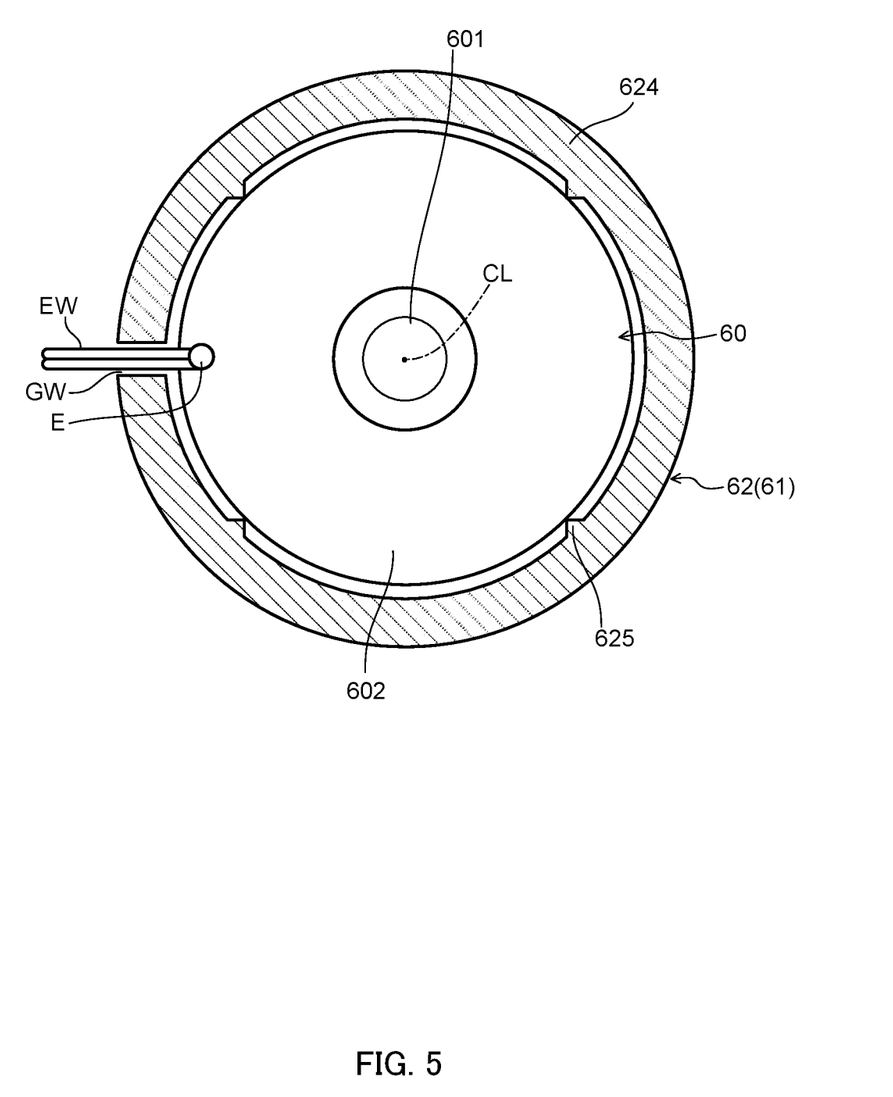
FIG. 5 is a sectional view taken along line V-V of FIG. 3.

Next, atomization device 100 is described with reference to FIGS. 2 to 5. FIG. 2 is a perspective view illustrating an example of an external appearance of atomization device 100. Note that 60 in FIG. 2 represents a diaphragm that atomizes the decontamination liquid in atomization device 100 through vibration. Diaphragm 60 is elaborated later. FIG. 3 is a sectional view of atomization device 100 taken along a vertical plane including central axis CL of diaphragm 60. FIG. 4 is a diagram illustrating an example of external appearances of diaphragm 60 and holding member 61. FIG. 5 is a sectional view taken along line V-V of FIG. 3. The following description assumes that the decontamination liquid used for the decontamination operation of culture device 1 is hydrogen peroxide solution.

Atomization device 100 includes main body part 2, lid 3, supporting member 4, leg 5 and atomization mechanism 6.

Main body part 2 includes liquid supplying reservoir 71R described later, and hydrogen peroxide solution is stored in storage space SR (see FIG. 3), which is a space surrounded by liquid supplying reservoir 71R.

Depression 21 is formed in the front outer surface of main body part 2. Atomization mechanism 6 is disposed in depression 21. Depression 21 includes bottom surface 21S, which is a contact surface with which holding member 61 (described later) that makes up atomization mechanism 6 makes contact. Outlet OH is formed in main body part 2. Outlet OH, with a through hole that opens at bottom surface 21S, is a passage hole through which the hydrogen peroxide solution that flows out of storage space SR passes. Bottom surface 21S is a surface located on the rearmost side in depression 21. In bottom surface 21S, two liquid-stopping protrusions 22a and 22b are formed.

Liquid-stopping protrusions 22a and 22b protrude toward inner holding member 62 described later, and are in contact with inner holding member 62. As viewed from the front side, liquid-stopping protrusions 22a and 22b have annular shapes surrounding outlet OH. Liquid-stopping protrusion 22b has an inner diameter smaller than that of liquid-stopping protrusion 22a, and is located inside liquid-stopping protrusion 22a.

In addition, liquid level detection device 7 is provided inside main body part 2. Liquid level detection device 7 is elaborated later.

Lid 3 is a member that covers main body part 2 from the upper side. Supporting member 4 is a member attached on the lower side of main body part 2 and supports main body part 2.

Leg 5 is provided at the bottom surface of supporting member 4. Leg 5 includes a pair of front legs 51 on the front side, and a pair of rear legs 52 on the rear side. The size of front leg 51 in the vertical direction is greater than the size of rear leg 52 in the vertical direction. As such, in atomization device 100, the front end portion of supporting member 4 is located on the upper side than the rear end portion of supporting member 4 with respect to installation surface 1a. The inclination angle of supporting member 4 with respect to installation surface 1a is, for example, 6 degrees.

In addition, as viewed from the lateral side of atomization device 100, the lower side outline of front leg 51 includes a pointed portion and a curved portion, and front leg 51 is in substantially point contact with installation surface 1a. In addition, as viewed from the lateral side of atomization device 100, the lower side outline of rear leg 52 is curved, and rear leg 52 is in substantially point contact with installation surface 1a.

In this manner, the contact area between front leg 51 and installation surface 1a, and the contact area between rear leg 52 and installation surface 1a can be reduced as much as possible, and thus the hydrogen peroxide solution atomized by atomization device 100 can be diffused over a wide range of the region on the lower side of supporting member 4 in installation surface 1a.

Next, with reference to FIGS. 3 to 5, atomization mechanism 6 is described.

Atomization mechanism 6 includes diaphragm 60, holding member 61, and nozzle 64.

Diaphragm 60 includes jetting part 601 and nipped part 602. Jetting part 601 has a substantially dome shape protruding to the front side, and is located at the center portion of diaphragm 60. In jetting part 601, a plurality of through holes through which hydrogen peroxide solution passes is formed. Note that through holes are so small that they are not visible to the naked eye. Jetting part 601 vibrates back and forth under the vibration of nipped part 602. When jetting part 601 vibrates, the hydrogen peroxide solution is passed through the through holes and emitted in the form of minute droplets. That is, through the vibration of diaphragm 60, the hydrogen peroxide solution is atomized Jetting part 601 is made of metal, and is for example, made of nickel. Note that diaphragm 60 is disposed with holding member 61 such that the outer surface of diaphragm 60 faces the obliquely upper side by holding member 61. At this time, the inclination angle between central axis CL of diaphragm 60 and the horizontal surface is, for example, 6 degrees.

Nipped part 602 is the outer periphery portion of diaphragm 60. Nipped part 602 is made of piezoelectric ceramic. As illustrated in FIG. 4, electrode E is attached to nipped part 602. Nipped part 602 vibrates back and forth by the piezoelectric effect when an AC voltage is applied from the power source provided in atomization device 100 to electrode E through wiring EW.

Holding member 61 is composed of inner holding member 62 and outer holding member 63. Note that both inner holding member 62 and outer holding member 63 are made of silicon.

As illustrated in FIG. 4, inner holding member 62 has a substantially cylindrical shape. Inner holding member 62 is a member that supports diaphragm 60 from the inner surface side. Inner holding member 62 includes contact part 621, inner cylindrical part 622, inner supporting part 623, and surrounding part 624.

Contact part 621, with an annular plate shape, is a portion corresponding to the rear side wall in inner holding member 62, and is in contact with liquid-stopping protrusions 22a and 22b. As illustrated in FIG. 3, liquid-stopping protrusions 22a and 22b are depressed into contact part 621, and the portion in contact with liquid-stopping protrusions 22a and 22b in contact part 621 is elastically deformed and recessed.

Inner cylindrical part 622 is located between storage space SR and diaphragm 60, and protrudes to the rear side from the inner periphery side end portion of contact part 621. Supply path 62R is formed in inner cylindrical part 622. The storage space SR side end portion of inner cylindrical part 622 is inserted to outlet OH of main body part 2. In this manner, outlet OH and supply path 62R are connected to each other, and the hydrogen peroxide solution in storage space SR is guided to diaphragm 60 through outlet OH and supply path 62R.

Size X from the diaphragm 60 side end portion of inner cylindrical part 622 to the storage space SR side end portion of inner cylindrical part 622 is smaller than the minimum value of the inner diameter of inner cylindrical part 622.

FIG. 3 illustrates inner diameter Lmin, which represents a minimum value of the inner diameter of inner cylindrical part 622. In the present embodiment, inner diameter Lmin is the inner diameter at the diaphragm 60 side end portion of inner cylindrical part 622.

FIG. 3 illustrates the inner diameter of inner cylindrical part 622 gradually increasing toward storage space SR side. In FIG. 3, IUL represents the upper end line connecting the uppermost end of the inner peripheral surface of inner cylindrical part 622 at each position from the diaphragm 60 side end portion to the storage space SR side end portion. Upper end line IUL has a shape whose height with respect to installation surface 1a, which is a horizontal surface, increases toward storage space SR.

Inner supporting part 623 protrudes to the front side from the inner periphery side end portion of contact part 621. Inner supporting part 623 is located between diaphragm 60 and inner cylindrical part 622, and is in contact with the inner surface of nipped part 602 of diaphragm 60.

The cross-sectional shape of inner supporting part 623 taken along a plane including central axis CL of diaphragm 60 is rounded. In this manner, the inner surface of nipped part 602 and inner supporting part 623 are in contact with each other in an annular line form.

Surrounding part 624 is a cylindrical portion protruding to the front side from the outer peripheral end of contact part 621. As illustrated in FIG. 5, positioning protruding part 625, which protrudes toward the outer peripheral surface of diaphragm 60 and makes contact with the outer peripheral surface of diaphragm 60, is formed in the inner peripheral surface of surrounding part 624. Positioning protruding parts 625 are provided at four locations in the inner peripheral surface of surrounding part 624 at even intervals around central axis CL. In addition, positioning protruding part 625 has a shape with a pointed end. In addition, as illustrated in FIG. 4, wiring groove GW for inserting wiring EW of diaphragm 60 is formed in surrounding part 624.

Outer holding member 63 has a substantially annular plate shape. Outer holding member 63 is a member that supports diaphragm 60 from the outer surface side. Outer holding member 63 includes outer supporting part 631 protruding to the rear side from the inner periphery side end portion of outer holding member 63. Outer supporting part 631 is located between nozzle 64 and diaphragm 60, and is in contact with the outer surface of nipped part 602 of diaphragm 60. Jetting path 63R is formed in outer supporting part 631. The hydrogen peroxide solution atomized by diaphragm 60 passes through jetting path 63R.

The cross-sectional shape of outer supporting part 631 taken along a plane including central axis CL is rounded. In this manner, the outer surface of nipped part 602 and outer supporting part 631 are in contact with each other in an annular line form.

Next, nozzle 64 is described with reference to FIG. 3.

Nozzle 64 is a member in which through jetting hole 64H is formed. The hydrogen peroxide solution in a mist form past minute holes formed in diaphragm 60 passes through jetting hole 64H. The inner diameter of nozzle 64 increases as the distance from diaphragm 60 increases. In FIG. 3, OBL represents a lower end line connecting the lower end of the inner peripheral surface of nozzle 64 at each position from the diaphragm 60 side end portion to the end portion farthest from diaphragm 60. Lower end line OBL has a shape whose height with respect to installation surface 1a, which is a horizontal surface, decreases as the distance from diaphragm 60 increases.

The distance Y from the diaphragm 60 side end portion of nozzle 64 to the outer surface of diaphragm 60 is smaller than the minimum value of the inner diameter of nozzle 64. FIG. 3 illustrates inner diameter dmin, which represents a minimum value of the inner diameter of nozzle 64. In the present embodiment, inner diameter dmin is an inner diameter at the diaphragm 60 side end portion of nozzle 64.

Note that even when some droplets of the hydrogen peroxide solution generated by diaphragm 60 adhere to the outer surface of diaphragm 60 without passing through jetting path 63R, the adhered droplets can flow out of main body part 2 along the outer surface of diaphragm 60, the lower inner peripheral surface of outer holding member 63, and the lower inner peripheral surface of nozzle 64.

Next, liquid level detection device 7 is described with reference to FIG. 3.

Liquid level detection device 7 includes liquid reservoir 7R, connection tube CT, float F, and sensor Se.

Liquid reservoir 7R includes liquid supplying reservoir 71R and detecting reservoir 72R. Liquid supplying reservoir 71R stores the hydrogen peroxide solution to be supplied toward diaphragm 60.

Detecting reservoir 72R includes upper cylindrical part 721, lower cylindrical part 722, and tapered cylindrical part 723. Lower cylindrical part 722 and tapered cylindrical part 723 are formed of a transparent material. In FIG. 3, TCL represents the central axis of detecting reservoir 72R. Upper cylindrical part 721 is composed of upper portion 721A, lower portion 721B, and connecting portion 721C. Upper portion 721A is a topmost portion of upper cylindrical part 721, and is composed of the same material as liquid supplying reservoir 71R. Upper protrusion piece 721F protruding toward central axis TCL of detecting reservoir 72R is formed in the inner peripheral surface of upper portion 721A. Lower portion 721B is a lowermost portion of upper cylindrical part 721, and is formed integrally with tapered cylindrical part 723 and lower cylindrical part 722. Connecting portion 721C is, for example, a silicon tube, and connects between upper portion 721A and lower portion 721B connect.

Lower cylindrical part 722 is located on the lower side than upper cylindrical part 721. The inner diameter of lower cylindrical part 722 is smaller than the inner diameter of the upper cylindrical part, and greater than the outer diameter of float F. Lower protrusion piece 722F protruding toward central axis TCL of detecting reservoir 72R is formed in the inner peripheral surface of detecting reservoir 72R.

Note that the movable range of float F is between upper protrusion piece 721F and lower protrusion piece 722F.

Tapered cylindrical part 723 is portion located between upper cylindrical part 721 and lower cylindrical part 722. The inner diameter at the upper end of tapered cylindrical part 723 is the same as the inner diameter of upper cylindrical part 721, and the inner diameter at the lower end of tapered cylindrical part 723 is the same as the inner diameter of lower cylindrical part 722.

Connection tube CT is a bent tube. Connection tube CT is located on the lower side of liquid supplying reservoir 71R and detecting reservoir 72R. One end of connection tube CT is connected to liquid supplying reservoir 71R from the lower side, and the other end of connection tube CT is connected to detecting reservoir 72R from the lower side. In this manner, liquid supplying reservoir 71R is connected to detecting reservoir 72R through connection tube CT, and liquid level LS of the hydrogen peroxide solution in liquid supplying reservoir 71R and liquid level SS of the hydrogen peroxide solution in detecting reservoir 72R are at the same height.

Float F is disposed in detecting reservoir 72R, and floated on the hydrogen peroxide solution in detecting reservoir 72R. Thus, one of the height of liquid level SS and the height of float F is determined when the other is determined. Float F is composed of an opaque material.

Sensor Se is, for example, an optoelectronic sensor such as a photo-microsensor. Sensor Se is disposed on the lower side of tapered cylindrical part 723 to surround the periphery of lower cylindrical part 722. Sensor Se includes a light emission part (not illustrated in the drawing) and a light reception part (not illustrated in the drawing), and when the light emitted from the emission part toward the light reception part is blocked, sensor Se outputs a detection signal indicating the fact that the light from the light emission part is blocked. In the present embodiment, float F blocks the light from the light emission part. Specifically, when the light from the light emission part is not detected at the light reception part, the position of float F is detected, the position of liquid level SS is detected based on the detected position of float F. FIG. 3 illustrates sensor detection line SSL that represents a position higher than the through hole of diaphragm 60. The size of each portion of detecting reservoir 72R and the sizes of front leg 51 and rear leg 52 in the vertical direction are set such that float F reaches the position for blocking the light from the light emission part when liquid level SS reaches sensor detection line SSL.

Next, an operation of atomization device 100 during decontamination operation is described.

First, the user detaches lid 3 from main body part 2, fills storage space SR of atomization device 100 with the hydrogen peroxide solution, and attaches lid 3 to the upper part of main body part 2 to cover it. Next, the user disposes atomization device 100 at installation surface 1a by opening the door of culture device 1, and electrically connects atomization device 100 to culture device 1. When culture device 1 is connected to atomization device 100, culture device 1 can control atomization device 100.

Next, when the user turns on the power source of culture device 1 and performs a predetermined operation at an operation panel (not illustrated in the drawing) of culture device 1, culture device 1 turns on the power source of atomization device 100. When the power source of atomization device 100 applies an AC voltage to nipped part 602, nipped part 602 vibrates back and forth at a predetermined frequency.

When nipped part 602 vibrates, jetting part 601 vibrates back and forth in synchronization with the vibration of nipped part 602. When jetting part 601 vibrates back and forth, the hydrogen peroxide solution in contact with the inner surface of jetting part 601 enters the through hole, and is output to the outer surface side through the through hole (i.e., passed through the through hole). When the hydrogen peroxide solution passes through the through hole, minute droplets of the hydrogen peroxide solution are formed, and emitted (i.e., atomized) to culture chamber R. Note that the droplets generated by diaphragm 60 has a size corresponding to the size of the diameter of the through hole. That is, the size of the droplets to be generated can be changed by changing the size of the diameter of the through hole.

The hydrogen peroxide emitted to culture chamber R is sent to every corner of culture chamber R by an air blaster (not illustrated in the drawing) of culture device 1. The hydrogen peroxide emitted to culture chamber R is decomposed into hydroxyl radical and hydroxide ion. When the hydroxyl radical causes a chain reaction of taking electrons from contaminants in culture chamber R, the contaminants in culture chamber R are removed.

As the hydrogen peroxide solution in liquid supplying reservoir 71R is atomized by diaphragm 60, liquid level LS and liquid level SS are lowered. In addition, float F is also lowered as liquid level SS is lowered.

When a predetermined time elapses after the power source of atomization device 100 is turned on, culture device 1 stops the operation of the power source of atomization device 100. In this manner, the vibration of diaphragm 60 stops.

In this manner, the decontamination operation of culture device 1 is completed.

Note that in the case where liquid level LS reaches a predetermined position such as sensor detection line SSL before the predetermined time elapses, culture device 1 may stop the atomizing of the hydrogen peroxide solution at atomization device 100.

When liquid level LS, i.e., liquid level SS, reaches sensor detection line SSL, the light from the light emission part is blocked by float F, and the light reception part of sensor Se stops receiving the light from the light emission part. When light reception part stops receiving the light from the light emission part, sensor Se outputs a detection signal to culture device 1. When the detection signal from sensor Se is input, culture device 1 stops the operation of the power source of atomization device 100 to stop the vibration of diaphragm 60.

Note that when diaphragm 60 stops the vibration, at least all through holes of diaphragm 60 are immersed in the hydrogen peroxide solution.

According to the present embodiment, the through hole is formed in diaphragm 60, and, through vibration of diaphragm 60, the hydrogen peroxide solution that passes through the through hole is atomized. In this manner, atomization device 100 can generate the droplets of hydrogen peroxide solution with the size corresponding to the diameter of the through hole, and can reliably generate droplets with smaller sizes by reducing the size of the through hole. Note that in comparison with large droplets, small droplets are more likely to reach farther on air. Thus, atomization device 100 of the present embodiment can diffuse the hydrogen peroxide solution to every corner of culture chamber R. Thus, atomization device 100 of the present embodiment can effectively perform decontamination of culture chamber R.

The size, from storage space SR side end portion to the diaphragm 60 side end portion, of supply path 62R (i.e., inner cylindrical part 622) through which the hydrogen peroxide solution that goes toward diaphragm 60 from storage space SR passes is small. In this manner, since the bubbles generated on the inner surface side through the vibration of diaphragm 60 tend to move to storage space SR, the air layer generated by gathering the bubbles is not enlarged and the lower end of the air layer does not reach the through hole of diaphragm 60. Thus, a situation where the atomizing of the hydrogen peroxide solution is stopped due to the air layer reaching the inner surface side of the through hole can be prevented, and the atomizing operation can be effectively continued. Note that the smaller the size of inner cylindrical part 622 from the storage space SR side end portion to the diaphragm 60 side end portion, the more desirable.

In addition, at each position from the diaphragm 60 side end portion to the storage space SR side end portion, upper end line IUL connecting the uppermost end of the inner peripheral surface of inner cylindrical part 622 has the shape whose height increases toward storage space SR. Thus, the bubbles generated at the inner surface of diaphragm 60 through the vibration of diaphragm 60 are less retained at the upper side of supply path 62R, and are guided to storage space SR. Thus, a situation where the atomizing of the hydrogen peroxide solution is stopped due to the air layer formed of the bubbles reaching the inner surface side of the through hole can be prevented, and the atomizing operation can be effectively continued.

The distance from diaphragm 60 to the diaphragm 60 side end portion of nozzle 64 is small. In this manner, the hydrogen peroxide solution that has entered the space formed by diaphragm 60 and the lower inner peripheral surface of outer holding member 63 smoothly flows along the inner peripheral surface of nozzle 64 to the outside of main body part 2. Thus, a situation where the atomizing of the hydrogen peroxide is stopped due to the through hole blocked by the hydrogen peroxide solution on the outer surface side of diaphragm 60 can be prevented, and the atomizing operation can be effectively continued. Note that the smaller the distance from diaphragm 60 to the diaphragm 60 side end portion of nozzle 64, the more desirable.

In addition, since the lower end line OBL connecting the lower end of the inner peripheral surface of nozzle 64 at each position from the diaphragm 60 side end portion to the end portion farthest from diaphragm 60 has the shape whose height decreases as the distance from diaphragm 60 increases, the hydrogen peroxide solution more easily flows to the outside of main body part 2. Thus, the hydrogen peroxide solution is less retained on the outer surface side of diaphragm 60, and the atomizing operation can be effectively continued.

In main body part 2, liquid-stopping protrusions 22a and 22b are formed at bottom surface 21S of depression 21, which is a portion where atomization mechanism 6 is disposed, and liquid-stopping protrusions 22a and 22b are brought into contact with and depressed into contact part 621 of inner holding member 62 making up atomization mechanism 6. In this manner, in comparison with the case where atomization mechanism 6 and main body part 2 are brought into surface contact with each other, the leakage of the hydrogen peroxide solution from a portion between atomization mechanism 6 and main body part 2 can be reliably prevented.

At inner holding member 62, four positioning protruding parts 625 protruding toward the outer peripheral surface of diaphragm 60 are formed at even intervals around central axis CL. In this manner, in the plane where diaphragm 60 extends, diaphragm 60 can be held at a specific position. Further, since positioning protruding part 625 has a shape with a pointed end, the contact area with diaphragm 60 can be small. In this manner, inner holding member 62 does not press diaphragm 60 with more force than necessary, and thus damages such as buckling of diaphragm 60 can be prevented.

The cross-sectional shapes, along a plane including central axis CL of diaphragm 60, of inner supporting part 623 and outer supporting part 631 that sandwich diaphragm 60 are rounded. In this manner, diaphragm 60 is sandwiched in substantially line contact manner between inner supporting part 623 and outer supporting part 631. Thus, the vibration of nipped part 602 to which an AC voltage is applied from the power source is easily transmitted to jetting part 601. That is, jetting part 601 can be more effectively vibrated, and the hydrogen peroxide solution can be efficiently atomized.

Since the size of front leg 51 in the vertical direction is greater than the size of rear leg 52 in the vertical direction, diaphragm 60 can be disposed such that its outer surface faces the obliquely upper side. Thus, the hydrogen peroxide solution atomized by diaphragm 60 can be delivered farther. In this manner, the hydrogen peroxide solution can be more easily diffused to culture chamber R.

Modification

In the above-described embodiment, inner holding member 62 satisfies both the following (a) and (b), but as long as at least one of (a) and (b) is satisfied, a situation where the atomizing of the hydrogen peroxide solution is stopped due to the air layer formed by the bubbles generated on the inner surface side of diaphragm 60 can be prevented and the atomizing operation can be effectively continued.

(a) The size of inner cylindrical part 622 from the storage space SR side end portion to the diaphragm 60 side end portion is small as much as possible.

(b) Upper end line IUL of inner cylindrical part 622 has the shape whose height increases toward storage space SR.

The inner diameter of outer supporting part 631 of outer holding member 63 may be increased as the distance from diaphragm 60 increases. In this case, the inner diameter of outer supporting part 631 at the end portion on the side remote from diaphragm 60 may be the same as the inner diameter of the diaphragm 60 side end portion of nozzle 64. In this case, the hydrogen peroxide solution on the outer surface side of diaphragm 60 more easily flows to the outside of main body part 2.

The liquid-stopping protrusion may be formed at contact part 621 of inner holding member 62. In this case, the liquid-stopping protrusion protrudes toward bottom surface 21S of main body part 2, and makes contact with bottom surface 21S. Note that when atomization mechanism 6 is disposed at depression 21 in the case where the liquid-stopping protrusion is formed at contact part 621 of inner holding member 62, the liquid-stopping protrusion is elastically deformed and crushed between contact part 621 and bottom surface 21S.

The number of positioning protruding parts 625 is not limited as long as three or more positioning protruding parts 625 are formed.

In addition, positioning protruding part 625 may not be in contact with diaphragm 60. In this case, even when the positional displacement of diaphragm 60 in the plane where diaphragm 60 extends is caused due to the vibration of diaphragm 60, the positionally displaced diaphragm 60 makes contact with positioning protruding part 625, and thus the positional displacement of diaphragm 60 can be suppressed within a certain range. In addition, since diaphragm 60 is not in contact with all positioning protruding parts 625 at all times, diaphragm 60 can be held without pressing diaphragm 60 from its outer periphery side. Thus, the load applied to diaphragm 60 can be reduced.

In addition, inner holding member 62 may not include surrounding part 624, and alternatively, outer holding member 63 may include a portion corresponding to surrounding part 624. In this case, at this portion, a positioning protruding part is formed.

This application is a continuation of International Patent Application No. PCT/JP2020/038225, filed on Oct. 9, 2020, the disclosure of which is incorporated herein by reference in its entirety. International Patent Application No. PCT/JP2020/038225 is entitled to (or claims) the benefit of Japanese Patent Application No. 2019-197487, filed on Oct. 30, 2019, the disclosure of which is incorporated herein by reference in its entirety.

INDUSTRIAL APPLICABILITY

The atomization device according to the present disclosure is applicable to decontamination operations of culture devices. Therefore, its industrial applicability is wide.

REFERENCE SIGNS LIST

1 Culture device
R Culture chamber
100 Atomization device
2 Main body part
21 Depression
21S Bottom surface
22*a*, 22*b* Liquid-stopping protrusion
OH Outlet
3 Lid
4 Supporting member
5 Leg
51 Front leg
52 Rear leg
6 Atomization mechanism
60 Diaphragm
E Electrode
EW Wiring
601 Jetting part
602 Nipped part
61 Holding member
62 Inner holding member
621 Contact part
622 Inner cylindrical part
623 Inner supporting part
624 Surrounding part
625 Positioning protruding part
62R Supply path
IUL Upper end line
GW Wiring groove
63 Outer holding member
631 Outer supporting part
63R Jetting path
64 Nozzle
64H Jetting hole
OBL Lower end line
CL Central axis
SR Storage space
7 Liquid level detection device
7R Liquid reservoir
71R Liquid supplying reservoir
LS Liquid level
72R Detecting reservoir
SS Liquid level
721 Upper cylindrical part
721A Upper portion
721B Lower portion
721C Connecting portion
721F Upper protrusion piece
722 Lower cylindrical part
722F Lower protrusion piece
723 Tapered cylindrical part
CT Connection tube
TCL Central axis
SSL Sensor detection line
F Float
Se Sensor

The invention claimed is:

1. An atomization device comprising:

a main body part including a storage space configured to store hydrogen peroxide solution;

a diaphragm including a jetting part configured to atomize hydrogen peroxide solution that passes through a through hole, the through hole being formed in the jetting part of the diaphragm and a part through which the hydrogen peroxide solution stored in the storage space passes, the diaphragm including an outer surface facing a side opposite to a storage space side, the diaphragm being disposed on a front side of the main body part such that the outer surface faces an obliquely upper side with respect to a horizontal surface; and a holding member including an inner cylindrical part and a contact part configured to make contact with the main body part, wherein the inner cylindrical part located between the storage space and the diaphragm and including a supply path connected to the storage space, the supply path being a part through which hydrogen peroxide solution flowing from the storage space toward the diaphragm passes, wherein an upper end line connecting an uppermost end of an inner peripheral surface of the inner cylindrical part at each position from an end portion on a diaphragm side to an end portion on a storage space side has a shape whose height increases as a distance to the storage space decreases, wherein the jetting part has a dome shape protruding to the front side of the main body, wherein the main body part includes a bottom surface to which the contact part makes contact, and wherein a liquid-stopping protrusion is formed in one of the contact part and the bottom surface, the liquid-stopping protrusion protruding toward the other of the contact part and the bottom surface and configured to make contact with the other of the contact part and the bottom surface.

2. The atomization device according to claim 1, further comprising a front leg located on a lower side of the main body part, and configured to support a front side of the main body part; and a rear leg located on a lower side of the main body part, and configured to support a rear side of the main body part, wherein a size in a vertical direction of the rear leg is smaller than that of the front leg.

3. The atomization device according to claim 1, wherein in the main body part, an outlet through which the hydrogen peroxide solution that flows out to outside of the storage space passes is formed, and wherein the supply path is connected to the outlet.

4. The atomization device according to claim 1, wherein a size from an end of the inner cylindrical part on a diaphragm side to an end of the inner cylindrical part on a storage space side is smaller than a minimum value of an inner diameter of the inner cylindrical part.

5. The atomization device according to claim 1, wherein the holding member includes a positioning protruding part protruding toward an outer peripheral surface of the diaphragm.

6. The atomization device according to claim 1, wherein the holding member further includes an inner supporting part located between an end of the inner cylindrical part on a diaphragm side and the diaphragm, and an outer supporting part configured to make contact with the outer surface, the inner supporting part being configured to make contact with an inner surface of the diaphragm, the inner surface facing a storage space side, wherein an outer periphery portion of the diaphragm is sandwiched by the inner supporting part and the outer supporting part, wherein an outline of the inner supporting part on an inner surface side in a cross-sectional shape taken along a plane including a central axis of the diaphragm is rounded, and wherein an outline of the outer supporting part on an outer surface side in a cross-sectional shape taken along the plane is rounded.

7. The atomization device according to claim 1, further comprising a nozzle having an inner diameter that increases as a distance from the diaphragm increases and including a jetting hole formed in the nozzle, the jetting hole being a part through which the hydrogen peroxide solution past the through hole passes, wherein a distance from the diaphragm to an end portion of the nozzle on a diaphragm side is smaller than a minimum value of an inner diameter of the nozzle, and wherein hydrogen peroxide solution adhered on the outer surface flows along an inner peripheral surface of the nozzle to outside of the main body part.

8. The atomization device according to claim 7, wherein a lower end line connecting a lower end of an inner peripheral surface of the nozzle at each position from an end portion on a diaphragm side to an end portion on a side farthest from the diaphragm has a shape whose height decreases as a distance from the diaphragm increases.

9. The atomization device according to claim 1, comprising the hydrogen peroxide solution stored in the storage space.

10. A culture device comprising the atomization device according to claim 1.

* * * * *